United States Patent [19]

Ogawa et al.

[11] Patent Number: 4,552,841
[45] Date of Patent: Nov. 12, 1985

[54] N-ACETYL-β-D-GLUCOSAMINIDES FOR DETERMINING N-ACETYL-β-D-GLUCOSAMINIDASE ACTIVITY

[75] Inventors: Yasunao Ogawa; Akira Noto, both of Osaka; Sachio Mori, Hyogo; Mitsuru Yoshioka, Osaka, all of Japan

[73] Assignee: Shionogi & Co., Ltd., Osaka, Japan

[21] Appl. No.: 487,703

[22] Filed: Apr. 21, 1983

Related U.S. Application Data

[62] Division of Ser. No. 357,317, Mar. 11, 1982, Pat. No. 4,433,139.

[51] Int. Cl.$^4$ ............................................. G01N 31/14
[52] U.S. Cl. ...................... 435/18; 435/810; 422/61
[58] Field of Search ................ 422/61; 435/18, 810

[56] References Cited

U.S. PATENT DOCUMENTS 3,699,005 10/1972 Foster .................................... 435/21
3,968,011 7/1976 Manautou et al. .................... 435/18
4,152,513 5/1979 Austin et al. ........................ 536/17.2
4,433,139 2/1984 Ogawa et al. ...................... 536/17.2

FOREIGN PATENT DOCUMENTS 2453069 5/1976 Fed. Rep. of Germany ....... 536/4.1

OTHER PUBLICATIONS

*Clinical Chemistry*, Noto et al., "Simple Rapid Spectrophotometry of Urinary N-Acetyl-β-D Glucosaminidase with Use of a New Chromogenic Substrate", vol. 29, No. 10, 1983, pp. 1713-1716.

Primary Examiner—Barry S. Richman
Assistant Examiner—John Donofrio
Attorney, Agent, or Firm—Wenderoth, Lind & Ponack

[57] ABSTRACT

N-Acetyl-β-D-glucosaminides produced from 1-chloro-1-deoxy-2,3,4,6-tetraacetyl-α-D-glucosamine and indicators for titration as the aglycons useful as substrates in kits for diagnostic aid, with which N-acetyl-β-D-glucosaminidase activity can be determined colorimetrically in high sensitivity, precisely, and quickly.

1 Claim, 2 Drawing Figures

N-ACETYL-β-D-GLUCOSAMINIDES FOR DETERMINING N-ACETYL-β-D-GLUCOSAMINIDASE ACTIVITY

This application is a division of application Ser. No. 357,317, filed Mar. 11, 1982 (now U.S. Pat. No. 4,433,139).

BACKGROUND OF THE INVENTION

N-Acetyl-β-D-glucosaminidase (abbreviated to as NAGase) is an enzyme in lysosome which is contained abundantly in the renal tubular epithelia and is related to the degradation of mucopolysaccharides and glycoproteins. It is recognized that the NAGase in urine increases in various cases of renal diseases or after an operation of the kidney and the NAGase in urine as well as serum increases in case of diabetes. In the field of clinical and animal experiments, the measurement of the NAGase has attracted an interest in connection with diagnosis of various renal diseases and also as an indicator in examining nephrotoxicity.

In the prior art, p-nitrophenyl N-acetyl-β-D-glucosaminide [Biochemical Preparations, 10, 118 (1963)] and 4-methylumbelliferyl-N-acetyl-β-D-glucosaminide [Clinica Chimica Acta, 69(1), 85–91 (1976)] have generally been used in the determination of the NAGase activity. The use of the former, however, has a disadvantage that biocomponents such as billirubin and hemolytic hemoglobin interfere with the measurement at the wavelength employed to require the blank measurement for each sample and so complicate the measurement procedure. The use of the latter has also a disadvantage that special apparatus such as a spectrophotometer are needed. The present inventors have completed this invention as the result of intensive investigations to find substrates for determining the NAGase activity with which the measurement can be performed in high sensitivity, precisely and quickly without the disadvantages mentioned above. It has been described in Jap. Pat. Unexam. Pub. No. 51-114990, etc., that phenolphthaleinyl N-acetyl-β-D-glucosaminide structurally analogous to the compounds of the present invention can be used in determining the NAGase in saliva of pregnant women. This reagent, however, has disadvantages that it is insoluble in the assay buffer and even after solubilization with a solubilizing agent, the assay reaction yields unstable color which is liable to fade soon. The compounds of the present invention have no such disadvantages.

BRIEF SUMMARY OF THE INVENTION

The present invention relates to novel N-acetyl-β-D-glucosaminides, to a method for determining the N-acetyl-β-D-glucosaminidase activity, and to kits therefor.

The novel N-acetyl-β-D-glucosaminides of the present invention are easily produced from 1-chloro-1-deoxy-2,3,4,6-tetraacetyl-β-D-glucosamine and the corresponding aglycon, and are used as substrates for determining the NAGase activity in urine or serum collected from human or animals. In the present invention the NAGase activity is determined colorimetrically by using the kit consisting of a substrate reagent, a buffer agent, and an alkaline agent.

DETAILED DESCRIPTION

The novel N-acetyl-β-D-glucosaminides of the present invention have the general formula (I).

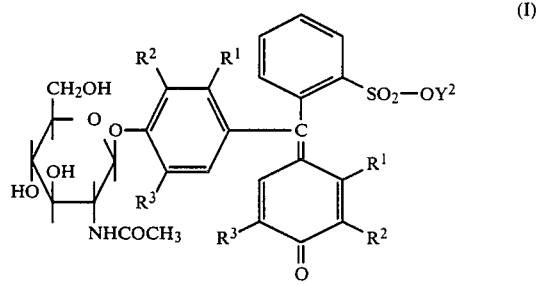

wherein each of $R^1$, $R^2$, and $R^3$ is hydrogen, a lower alkyl, or a halogen and $Y^2$ is an alkali metal.

In the formula (I) in the above definition, the lower alkyl represented by $R^1$, $R^2$, and $R^3$ means a straight or branched chain alkyl of 1–4 carbon atoms such as methyl, ethyl, propyl, isopropyl, butyl, and isobutyl, and particularly methyl and isopropyl are preferred. The halogen means fluoro, chloro, bromo, or iodo, and particularly chloro or bromo is preferred. The alkali metal represented by $Y^2$ means lithium, sodium, or potassium.

The compounds (I) of the present invention are easily produced from 1-chloro-1-deoxy-2,3,4,6-tetraacetyl-β-D-glucosamine represented by the formula (II) and an aglycon represented by the formula (III).

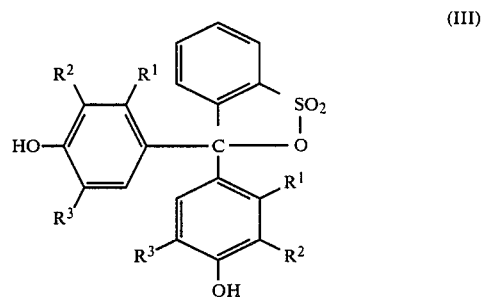

wherein each of $R^1$, $R^2$, and $R^3$ has the same meaning as mentioned above and Ac is acetyl.

The compound (II) is known and has been described in Biochemical Preparations 10, 118 (1963).

The compound (III) is selected from commercially available indicators for titration, which turn red or purple~blue in an alkaline solution (about pH 10-11), such as phenol red (phenolsulfonphthalein) [$R^1=R^2=R^3=H$], cresol red (o-cresolsulfonphthalein) [$R^1=R^2=H, R^3=CH_3$], meta-cresol purple (m-cresolsulfonphthalein) [$R^1=CH_3, R^2=R^3=H$], chlorophenol red (dichlorophenolsulfonphthalein) [$R^1=R^2=H, R^3=Cl$], etc., and particularly phenol red and meta-cresol purple are preferred. All of the above aglycons have an absorption maximum at a wavelength beyond 550 nm, and no measurement of blanks on specimens is required.

The compounds of the present invention may be produced according to the following reaction sequence.

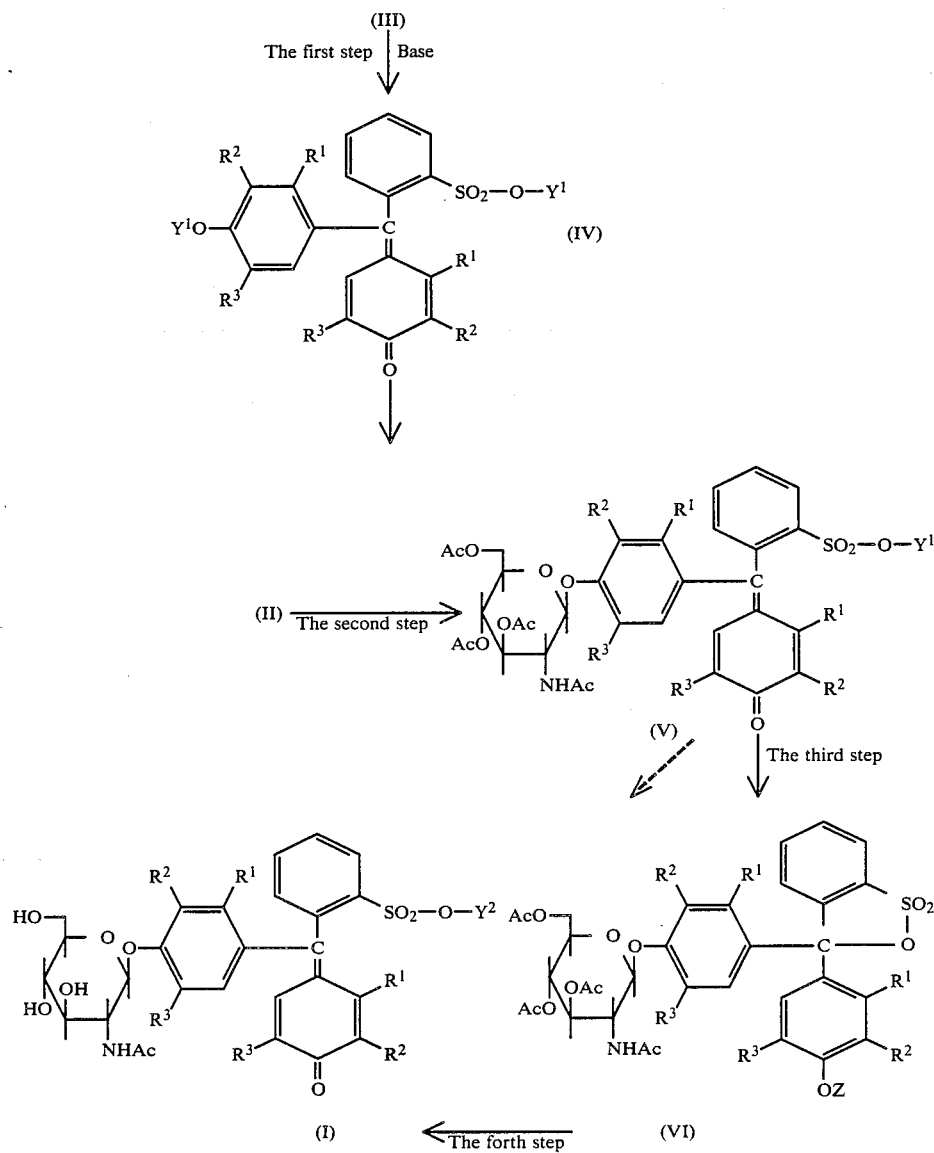

wherein each of $R^1$, $R^2$, $R^3$, and Ac is the same as the above, $Y^1$ and $Y^2$ are alkali metals, and Z is acyl. (The first step)

This step comprises cleavage of the sultone ring in the compound (III) to yield its di-alkali metal salt, and the reaction is easily achieved on base treatment. It is adequate to use an alkali metal hydroxide or alcoholate as the base. For example, lithium hydroxide, sodium hydroxide, potassium hydroxide, sodium methylate, sodium phenolate, etc. may be used, and particularly sodium hydroxide and sodium methylate are preferred.

Alternatively, instead of the above stepwise reaction, the reaction of the compound (II) with (III) may be carried out in the presence of a base in a proper solvent, preferably in a polar solvent, more preferably in acetone to yield the compound (V). (The second step)

This step comprises forming an ether linkage which is achieved by the reaction of the compound (II) with (IV). As the solvent, acetone, dimethylformamide, dimethylsulfoxide, etc. can be used. Particularly preferably dimethylformamide is employed under anhydrous conditions. The reaction can be carried out at room temperature or under cooling and is generally completed within ten and several hours generally.

After the termination of the reaction, the product is separated from the unchanged starting compound (IV) easily on acid treatment. As the acid, a weak acidic and cationic exchange resin like Amberlite ®IRC-50 (Rohm & Haas Co.) may be used besides inorganic acids like dilute hydrochloric acid, dil. sulfuric acid, and dil. nitric acid. (The third step)

This step comprises acylation of the product (V) from the second step for the purpose of purification, but this step may be omitted when feasible depending on the kind of aglycon and reaction conditions. As for the acylation, acetylation is particularly preferable and the reaction may be carried out with an equimolar or slightly excess amount of acetic anhydride in an adequate solvent, preferably in pyridine. Generally the reaction is completed within ten and several hours at room temperature. (The forth step)

In this step the acetyl groups except the N-acetyl group (the O-acetyl groups) or the alternative O-protecting groups are eliminated, and the reaction is achieved on base treatment. As the base, an alcoholate of alkali metal is adequate and particularly sodium methylate is preferred. The reaction is usually operated under cooling, preferably at a temperature of 0°–10° C., and is completed within ten and several hours.

After the termination of the reaction the product is treated with an acid to remove the excess base.

It is possible to carry out each step mentioned above in a single reaction vessel. For example, the compound (III) is treated with an alkali, the compound (II) is added, and then the acetyl is removed by alkali hydrolysis followed by acid treatment to give the compound (I).

The kit for determination of NAGase in this invention consists of the following articles.
  (i) A substrate reagent consisting of the compound (I) in this invention
  (ii) A buffer agent
  (iii) An alkaline agent The substrate reagent in (i) means the substrate itself which is the compound (I) or a mixture of the compound (I) and borax. It is preferred that this reagent is lyophilized, stored in tightly closed ampoules or vials and dissolved in a buffer solution immediately before use for maintaining a specified pH range, that is, a buffer in (ii).

The buffer agent in (ii) means an agent with which the pH range in the reaction of NAGase in maintained at 3.5–6.0, more preferably 4.0–5.5. For example, a citrate buffer, a borax-citrate buffer, a citrate-phosphate buffer, etc. dissolved in distilled water can be used. In case of using a borax-citrate buffer, which is especially preferred, the reaction of the substrate with NAGase proceeds linearly with time for the first 30 minutes at 37° C. while hydrolysis of the substrate is suppressed, whereby the absorbance of the substrate blank is lowered and the limit for determining NAGase is broadened. In case of using the substrate reagent mixed with borax, the same effects can be achieved by using the citrate buffer. The use of citrate-phosphate buffer is limited to urine, because the lag-phase appears in the NAGase assay of serum.

The alkaline agent in (iii) means the agent which can adjust the final pH of the assay solution at 10–11. For example, sodium carbonate, potassium carbonate, sodium hydroxide, potassium hydroxide, borate-sodium carbonate etc. can be selected and they may be dissolved in distilled water immediately before use. To suppress the hydrolysis of the substrate, the borate-sodium carbonate buffer is especially preferred.

EFFECTS AND USES

The compounds (I) in the present invention are used as substrates for determining the NAGase activity in urine or serum collected from human or animals.

THE PRINCIPLE OF MEASUREMENT

When a specimen is incubated with the compound (I) used as the substrate for a specified period of time in a buffer solution maintaining the pH of the system acidic (pH 3.5–6.0, particularly 4.0–5.5), NAGase in the specimen hydrolyzes the substrate (I) to give the aglycon (VIII) and N-acetylglucosamine (VII) as shown in the following. The resulting mixture is adjusted at pH 10–11 with an alkaline solution in order to change the aglycon (VIII) into the colored di-alkali salt represented by the formula (IV), and the resulting color is colorimetrically measured with a spectrophotometer.

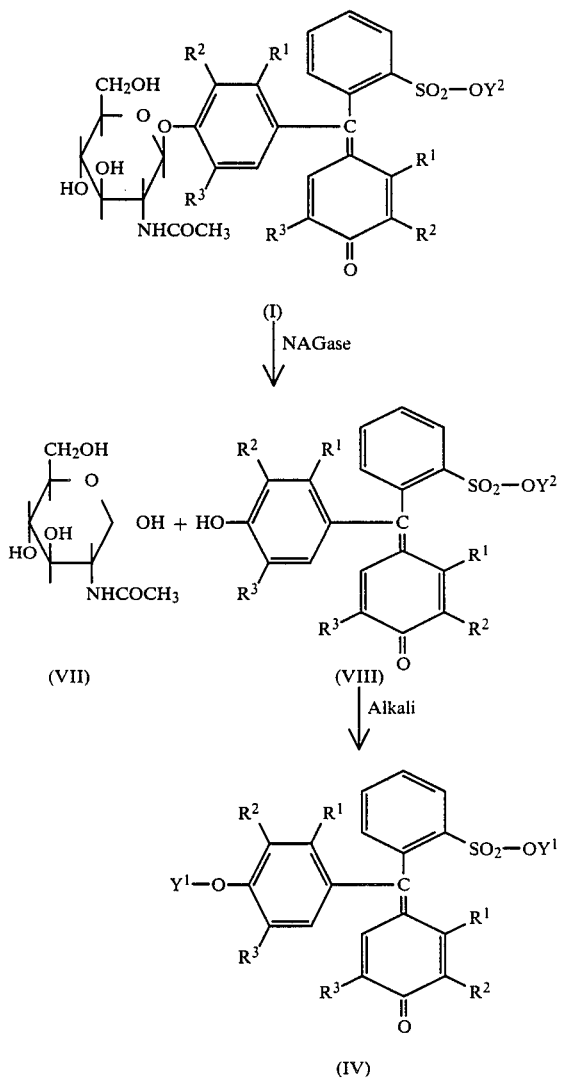

wherein each of $R^1$, $R^2$, $R^3$, $Y^1$, and $Y^2$ is the same as the above.

THE PROCEDURE FOR MEASUREMENT

In a 10 ml tube is placed 1.0 ml of the substrate solution (2–6 mM/L) and after preincubation at 37° C. for 5 minutes, 50 μl of a specimen* is added and the mixture is incubated at 37° C. for x minutes. After incubation the reaction is stopped by addition of 2.0 ml of the alkaline solution and the absorbance of the final solution is measured at the maximum absorption wavelength of the resulting aglycon within one hour using distilled water or air as the reference. The substrate blank can be obtained using 50 μl of distilled water instead of the specimen.

*Note: Specimen; urine or serum collected from human or animals, which preferably is measured immediately after collection. When the specimen is needed to be stored for a long period of time, its pH is adjusted to 6.5 with 2N-hydrochloric acid or 2N-potassium hydroxide. Under this condition, the NAGase activity in the specimen can be kept stable for one day at room temperature and for 4 months at −20° C.

Therein the amount of NAGase which produces 1 μmol of the aglycon (VIII) from (I) per minute is defined as 1 unit (u).

CALCULATION OF THE CONCENTRATION OF THE ENZYME

The concentration of NAGase in the specimen is calculated from the following equation.

Concentration of NAGase in specimen (u/L) =

$$\frac{\Delta E}{\epsilon \times d} \times 3.05 \times \frac{1}{x} \times \frac{1000}{0.05}$$

$E = E_1 - E_2$ $E_1$ = the absorbance of the final solution
$E_2$ = the absorbence of the substrate blank
d = the length of optical path (cm)
$\epsilon$ = the extinction coefficient (cm$^2$/μM) of the aglycon (VIII) at the wavelength employed
x = the reaction time (minute)

A period of 10–30 minutes and preferably 10–15 minutes is adequate in this assay.

STANDARD CURVE

As shown in the section "The procedure for measurement", a specified amount of NAGase is added to a substrate solution of the compounds (I) and the resulting mixture is allowed to react to yield the aglycon (VIII). Then the standard curve is made from the relationship between the aglycon amount (VIII) and the NAGase unit. For example, the activity of NAGase is determined with a kit which contains sodio-m-cresolsulfonphthaleinyl β-D-glucosaminide (I) (R$^1$=CH$_3$, R$^2$=R$^3$=H, Y$^2$=Na) (abbreviated as MCP-NAG) as the substrate and the relationship between the NAGase unit and the amount of liberated MCP [meta-cresol purple (m-cresolsulfonphthalein)] is obtained as shown in FIG. 1. FIG. 1 indicates that the determination of NAGase is possible at concentrations up to 200 u/L when MCP-NAG is the substrate.

PRECISION

The reproducibility of the assay is examined by multiple determinations using a specified NAGase solution: the variation coefficient is 1.95%, which indicates high reproducibility of this assay.

NORMAL VALUE

When the NAGase activity in urine is determined for 26 healthy persons (men: 14, women: 12) by the MCP-NAG method, the activities are 1.13–13.10 u/L for men and 0.68–5.20 u/L for women. It has been reported in Clinica Chimica Acta 73, 453 (1976) that the average activity is 8.1 u/L (1.5–29.8 u/L) for urine collected during 3 hours early in the morning.

COMPARISON WITH THE PRIOR ART

The NAGase activity from bovine kidney is determined by the known MCP-NAG method of the present invention in comparison with the method using p-nitrophenyl N-acetyl-β-D-glucosaminide as the substrate (the PNP-NAG method). FIG. 2 indicates the relationship between them. Wherein the determination of the activity of NAGase by the PNP-NAG method is carried out as follows.

In a 10 ml tube, 1.0 ml of the reagent-I solution[i] is placed and after preincubation for 10 minutes at 37° C., 50 μl of urine is added and the mixture is incubated at 37° C. After 30 minutes the reaction is stopped by addition of 2.0 ml of the reagent-II solution[ii]. Then within 2 hours the absorbance is measured at 405 nm using distilled water or air as the reference. In order to measure the urine blank required for each specimen, 1.0 ml of the reagent-III solution[iii] is used instead of the reagent-I solution and the procedure is operated in the same way. The substrate blank is obtained by carrying out the procedure using the reagent-I solution (1.0 ml), distilled water (50 μl), and the reagent-II solution (2.0 ml).

Notes: [i]5mM substrate solution (0.05M citrate-phosphate buffer, pH 4.40) [ii]0.2M borate-sodium carbonate buffer (pH 10.5) [iii]0.05M citrate-phosphate buffer (pH 4.40)

The concentration of NAGase in specimen is calculated from the following equation.

Concentration of NAGase in specimen (u/L)

Concentration of NAGase in specimen (μ/L) =

$$\frac{\Delta E \times 3.05}{18.19 \times d} \times \frac{1}{30} \times \frac{1000}{0.05} \quad \Delta E = E_1 - (E_2 + E_3)$$

$E_1$ = the absorbance of the final solution
$E_2$ = the absorbance of the urine blank
$E_3$ = the absorbance of the substrate blank
d = the length of optical path (cm)

As shown in FIG. 2, it is obvious that there is a good correlation between the MCP-NAG method and the PNP-NAG method. The activity determined by the MCP-NAG method, however, is higher by about 4% than the activity obtained by the PNP-NAG method conducted on the same specimen.

The following examples will demonstrate the present invention more in detail.

EXAMPLE 1

Sodio-phenolsulfonphthaleinyl-N-acetyl-β-D-glucosaminide

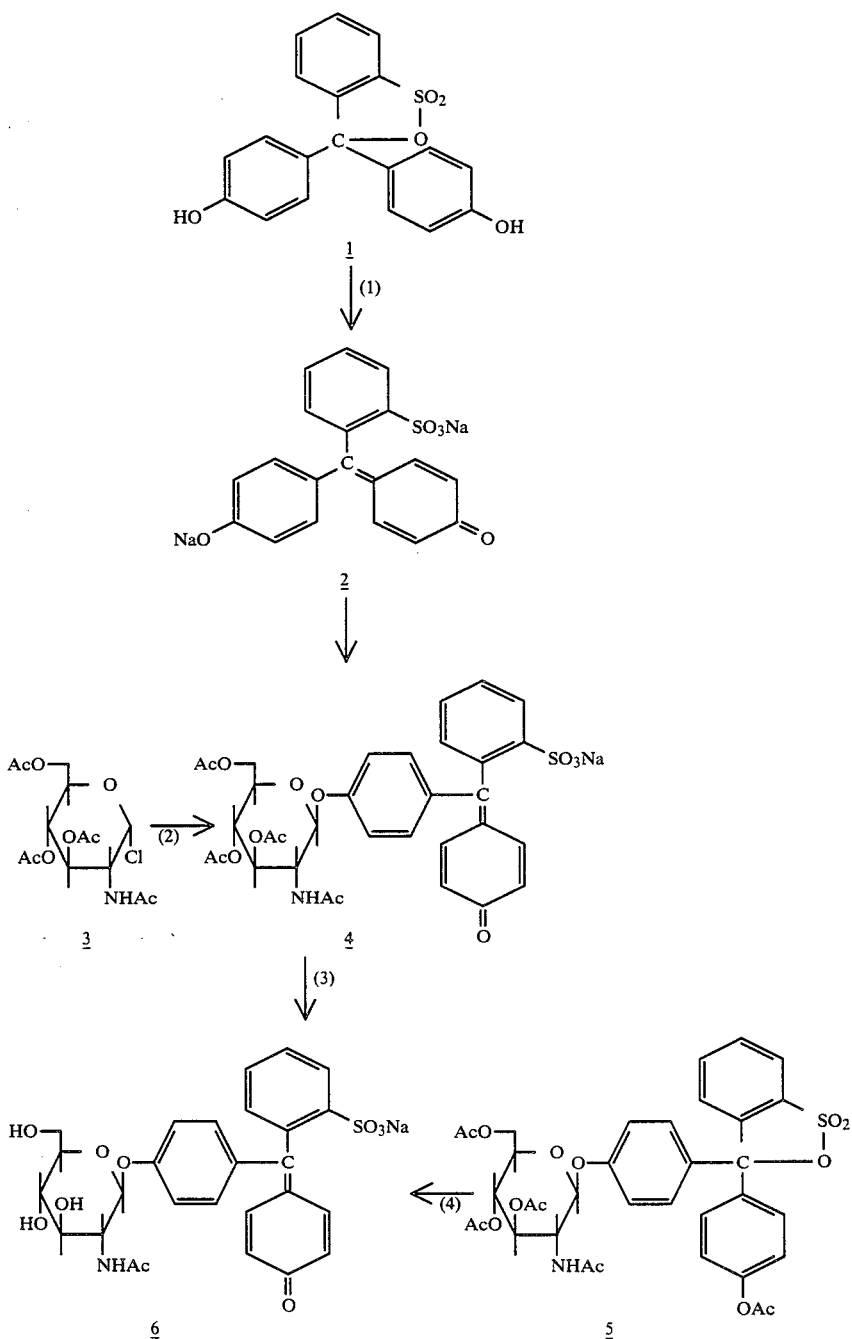

(1) In 1N methanolic sodium methoxide solution (2.0 ml, 2.0 mmol) is dissolved phenolsulfonphthalein 1 (373 mg, 1.05 mmol), and methanol is removed under reduced pressure at a temperature below 35° C. Benzene is added to the residue, the solid is ground, and the solvent is evaporated under reduced pressure at a temperature below 35° C. This procedure is repeated twice and the resulting residue is dried for 3 hours under reduced pressure to give the di-sodium salt 2 of phenolsulfonphthalein.

(2) The di-sodium salt 2 obtained in the above procedure is mixed with DMF (10 ml) as well as possible to give a bluish violet mixture. 1-Chloro-1-deoxy-2,3,4,6-tetraacetyl-α-D-glucosamine 3 (366 mg, 1.0 mmol) [Biochemical Preparations 10; 118 (1963)] is added under stirring to give a reddish violet nearly clear solution. The solution is stirred for about 30 minutes at room temperature and allowed to stand overnight (18 hours) at 5° C. Amberlite ®IRC-50 (2 ml) washed with methanol is added thereto and the mixture is stirred for 30 minutes, and filtered. The precipitate is washed with methanol. The filtrate and washings are combined and evaporated under reduced pressure. Toluene is added to the residue, and the solution is evaporated to dryness again under reduced pressure. The residue is dissolved in methanol and adsorbed on silica gel (3 g), and after removal of methanol, the residue is subjected to chromatography (stationary phase: 30 g silica gel; solvent system: ethyl acetate~ethyl acetate-methanol=3:1) to give a fraction (540 mg) containing sodio-phenolsulfonphthaleinyl-2,3,4,6-tetraacetyl-β-D-glucosaminide 4 as a principal component.

(3) To the fraction obtained in the above procedure (2) is added a mixture of acetic anhydride (4.5 ml) and pyridine (7 ml). After standing overnight, methanol (2 ml) is added under stirring and cooling. The resulting mixture is allowed to stand for 1 hour, and the solvent is removed under reduced pressure. Toluene is added to the residue and the mixture is evaporated to dryness under reduced pressure. This procedure is repeated twice and methylene chloride is added to the resulting residue in order to obtain a soluble fraction (about 540 mg). This fraction gives two main spots on thin layer chromatogram. Separation by column chromatography [stationary phase: silica gel (8.5 g), solvent system: benzene-ethyl acetate=1:2] gives O,O-diacetylphenolsulfonphthalein (first fraction) and O-acetylphenolsulfonphthaleinyl-2,3,4,6-tetraacetyl-β-D-glucosaminides 5 (second fraction) as an almost colorless foamy material. Yield, 42%.

The product 5 is further purified by column chromatography (stationary phase: silica gel, solvent system: benzene-ethyl acetate=1:2) to give a pure product 5.

IR: $\nu_{max}^{CHCl_3}$ 1750, 1689 cm$^{-1}$.

NMR: $\delta^{CDCl_3}$ 1.86(s,3H), 2.03(s,9H), 2.29(s,3H), 3.7–4.4(4H), 5.10(t,J=9.5 Hz, 1H), 5.36(d,J=8.0 Hz,1H), 5.43(t,J=9.5 Hz,1H), 6.24(d,J=9.0 Hz,1H), 6.8–8.0(12H).

$[\alpha]_d$ −6.3±0.3° (C=1.956, CHCl$_3$)

(4) In dry methanol (4 ml) is dissolved the product 5 (308 mg, 0.424 mmol) obtained in the above procedure (3), and 1N methanolic sodium methoxide solution (0.85 ml, 0.85 mmol) is added thereto. The resulting red solution is allowed to stand for 15 hours at 5° C. Amberlite ®IRC-50 (1.5 ml) moisted with methanol is added, and the mixture is stirred for 1.5 hours. The solid is collected by filtration and washed with methanol. The filtrate and washings are combined and evaporated under reduced pressure to give an orange powdery residue. This product is purified by column chromatography [stationary phase: silica gel (1.5 g), solvent system: ethyl acetate-methanol=2:1] to give sodio-phenolsulfonphthaleinyl N-acetyl-β-D-glucosaminide 6 (209 mg) as highly hydroscopic orange powder. Yield, 89%.

IR: $\nu_{max}^{KBr}$~3350(br), 1665(sh), 1625 cm$^{-1}$.

NMR: $\delta^{CD_3OD}$ 1.95(s,3H), 3.3–4.2(6H), 5.12(d,J=8.0 Hz,1H), 6.0–6.6(2H), 6.8–7.8(9H), 7.9–8.3(1H).

UV: $\lambda_{max}^{H2O}$ 262 nm($\epsilon$=10300), 408 nm($\epsilon$=22400) (C=16.94 μg/ml).

TLC (Merk precoated Kiesel Gel, ethyl acetate:methanol=2:1) Rf value: about 0.14.

$[\alpha]_D^{23}$ +35.9±0.8° (C=1.039, methanol).

EXAMPLE 2

Sodio-m-cresolsulfonphthaleinyl-N-acetyl-β-D-glucosaminide

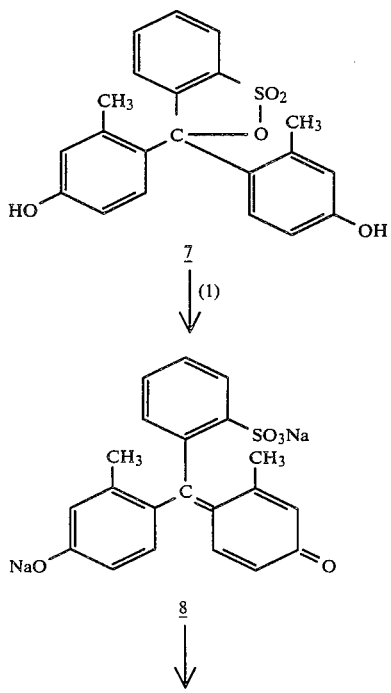

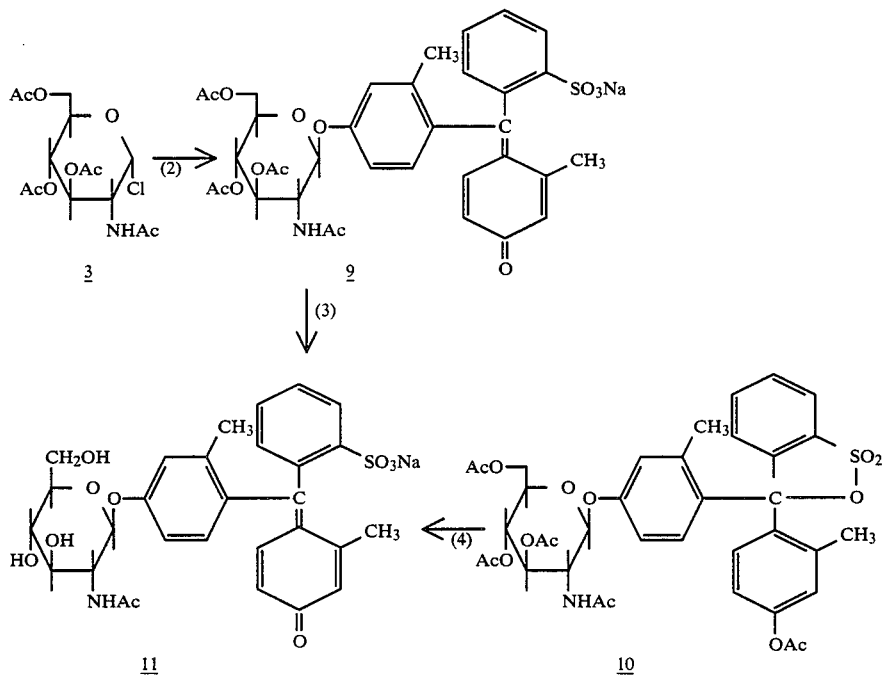

(1) According to the method described in example 1(1), di-sodium salt of m-cresolsulfonphthalein 8 is obtained from m-cresolsulfonphthalein 7 (4.02 g, 10.5 mmol) and 1N methandic sodium methoxide solution (20 ml, 20 mmol).

(2) The di-sodium salt 8 obtained above is mixed with DMF (50 ml) as well as possible, and then 1-chloro-1-deoxy-2,3,4,6-tetraacetyl-α-D-glucosamine 3 (3.66 g, 10 mmol) is added under stirring to give a reddish violet nearly clear solution. The solution is kept at 5° C. for 16.5 hours and when Amberlite ®IRC-50 (25 ml) moistened with methanol is added thereto, the color turns reddish brown. After stirring for 30 minutes, the mixture is filtered and the solid is washed with methanol. The filtrate and washings are combined and evaporated. Then DMF is removed by azeotropic distillation with toluene and the residue is dissolved in methanol (25 ml). The solution is mixed with silica gel (25 g), methanol is evaporated well, and the residue is subjected to column chromatography (stationary phase: silica gel). The fraction which is eluted with ethyl acetate (2.3 L) is discarded and subsequent elution with methanol (0.8 L) gives a fraction which contains sodio-m-cresolsulfonphthaleinyl-2,3,4,6-tetraacetyl-β-D-glucosaminide 9 as a principal component.

(3) To the fraction obtained in the above procedure (2) is added a mixture of acetic anhydride (50 ml) and pyridine (70 ml). After being kept overnight, the mixture is worked up in the same manner as described in example 1(3). The obtained residue gives two spots on thin layer chromatogram. Separation by column chromatography [stationary phase: silica gel (100 g), solvent system: benzene-ethyl acetate=1:2] gives O,O-diacetyl-m-cresolsulfonphthalein (first fraction) and O-acetyl-m-cresolsulfonphthaleinyl-2,3,4,6-tetraacetyl-β-D-glucosaminide 10 (4.50 g) (second fraction) as a light yellow foamy material. Yield, 60%.
IR: $\nu_{max}^{CHCl_3}$ 1747, 1688 cm$^{-1}$.

NMR: $\delta^{CDCl_3}$ 1.88(s,3H), 2.02(s,9H), 2.12(s,6H), 2.27(s,3H), 3.7-4.4(4H), 5.10(t,J=9.5 Hz,1H), 5.32(d,J=8.0 Hz,1H), 5.43(t,J=9.5 Hz,1H), 5.98(d,J=9.0 Hz,1H), 6.8-8.0(10H).
$[\alpha]_D^{24.5}$ 0.0 (C=0.977, CHCl$_3$)
$[\alpha]_{365}^{24.5}$ +2.8±0.4 (C=0.977, CHCl$_3$)

(4) In dry methanol (100 ml) is dissolved the product 10 (4.42 g, 5.86 mmol) obtained in the above procedure (3), and 1N methanolic sodium methoxide solution (11.72 ml, 11.72 mmol) is added thereto. The resulting dark brown solution is allowed to stand overnight at 5° C. Amberlite ®IRC-50 (30 ml) moistened with methanol is added and after stirring for 30 minutes, the mixture is filtered and washed with methanol. The filtrate and washings are combined and evaporated under reduced pressure. The resulting product is purified by column chromatography [stationary phase: silica gel (120 g), solvent system: ethyl acetate-methanol=2:1] to give sodio-m-cresolsulfonphthaleinyl-N-acetyl-β-D-glucosaminide 11 (2.77 g) as highly hygroscopic orange powder.
IR: $\gamma_{max}^{KBr}$ ~3400(br), 1660(sh), 1620 cm$^{-1}$.
NMR: $\delta^{CD_3OD}$ 1.6-2.4(9H), 3.3-4.2(6H), 4.9-5.2(1H), 5.9-8.4(10H).
$[\alpha]_D^{23.5}$ +52.6±0.9° (C=1.032, CH$_3$OH)
UV and VISIBLE: $\lambda_{max}^{H_2O}$ 269 nm($\epsilon$=12,200), 414 nm($\epsilon$=24,000) (C=11.80 μg/ml)

EXAMPLE 3

A lyophilized product of MCP-NAG and borax is dissolved in 0.05M citrate buffer (pH 4.15, 50 ml) to prepare substrate solution (the concentration of MCP-NAG 5.13mM, pH 4.4). In a 10 ml tube, 1.0 ml of the substrate solution is placed, and after preincubation at 37° C. for 5 minutes, urine (50 μl) is added thereto. The resulting solution is incubated at 37° C. After incubation for 15 minutes, a 0.3M sodium carbonate solution (2.0 ml) is added thereto to develop color of the liberated MCP, and the absorbance at 580 nm (E$_1$) is measured within 1 hour using distilled water or air as the reference. As a susbtrate blank, distilled water (50 μl) is added instead of the specimen to measure the absorbance (E₂). The concentration of NAGase is calculated as follows.

Concentration of NAGase (μ/L)

$$= \frac{\Delta E}{38 \times 1} \times 3.05 \times \frac{1}{15} \times \frac{1000}{0.05}$$

$$= \Delta E \times 107.0$$

EXAMPLE 4

A lyophilized product of sodio-phenolsulfonphthaleinyl N-acetyl-β-D-glucosaminide (PR-NAG) is dissolved in 0.05M borax-citrate buffer (pH 4.4) (5mM) to prepare a substrate solution. In a 10 ml tube, 1.0 ml of the substrate solution is placed, and after preincubation for 5 minutes at 37° C., human serum (50 μl) is added followed by immediate stirring. The resulting mixture is incubated at 37° C. for 10 minutes, and a 0.2M borate-sodium carbonate buffer (pH 10.5, 2.0 ml) is added to inactivate the enzyme and develop color of the liberated PR [phenol red (phenolsulfonphthalein)] concurrently. The absorbance at 557 nm (E₁) is measured using distilled water or air as the reference. As a substrate blank, distilled water (50 μl) is used instead of serum to measure the absorbance (E₂). The concentration of NAGase is calculated as follows.

Concentration of NAGase (μ/L)

$$= \frac{\Delta E}{63 \times 1} \times 3.05 \times \frac{1}{10} \times \frac{1000}{0.05}$$

$$= \Delta E \times 96.8$$

EXAMPLE 5

PR-NAG is dissolved in a 0.25M borax-citrate buffer (pH 4.4) so as to prepare a 25mM solution. The resulting solution is divided into 10-ml portions which are filled in 50 ml glass vials and then lyophilized. Boric acid (93.7 g) and sodium carbonate (706.3 g) are ground, mixed, and sieved. Then each 1.98 g of the mixture is packaged in a 120 ml polyethylene bottle with a powder filling machine.

EXAMPLE 6

The lyophilized PR-NAG product obtained in example 5 is dissolved in distilled water (50 ml) and 1 ml of the resulting solution is employed as a substrate solution. Distilled water (100 ml) is added to the powder contained in the polyethylene bottle obtained in example 5, and 2.0 ml of the solution is employed as an alkaline solution. The substrate solution and alkali solution are used for the assay procedure performed in the same manner as described in example 4. The concentration of NAGase is calculated as follows.

Concentration of NAGase (μ/L)

$$= \frac{\Delta E}{63 \times 1} \times 3.05 \times \frac{1}{10} \times \frac{1000}{0.05}$$

$$= \Delta E \times 96.8$$

EXAMPLE 7

The lyophilized MCP-NAG product which is produced in the same manner as described in example 5 is dissolved in distilled water (50 ml) and 1 ml of the solution is employed as a substrate solution. Distilled water (100 ml) is added to the powder contained in the polyethylene bottle obtained in example 5, and 2 ml of the solution is employed as an alkaline solution. The substrate solution and alkaline solution are used for the assay procedure performed in the same manner as described in example 3. The absorbence is measured at 580 nm:

Concentration of NAGase (μ/L)

$$= \frac{\Delta E}{38.2 \times 1} \times 3.05 \times \frac{1}{15} \times \frac{1000}{0.05}$$

$$= \Delta E \times 106.46$$

Figure 1:
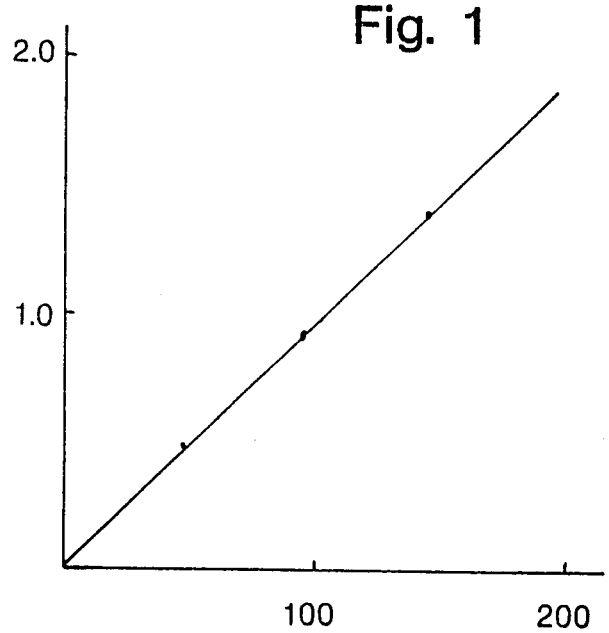
FIG. 1 shows the relationship between NAGase activity and liberated MCP in the MCP-NAG method. The horizontal axis indicates the concentration of NAGase (u/L), and the vertical axis indicates the amount of liberated MCP (ΔE 580 nm/15 min.). This figure shows that the determination of NAGase activity by the MCP-NAG method is possible at concentrations up to 200 u/L.
Figure 2:
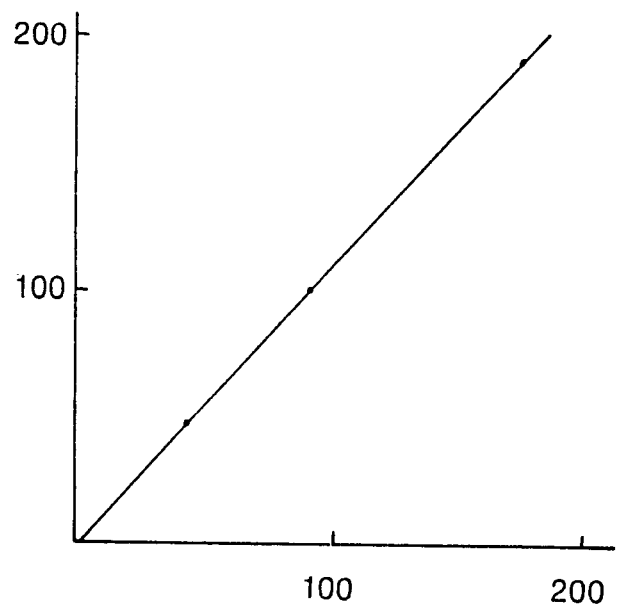
FIG. 2 shows the correlation between the PNP-NAG method and the MCP-NAG method. The horizontal axis indicates the concentration of NAGase (u/L) by the PNP-NAG method, and the vertical axis indicates that (u/L) by the MCP-NAG method.

Linear regression $$Y = 1.04X + 0.02$$

$$r = 0.9997$$

What is claimed is:

1. A kit for diagnostic aid consisting of the following articles
   (i) a substrate reagent which is a lyophilized product of sodio-m-cresolsulfonphthaleinyl N-acetyl-β-D-glucosaminide;
   (ii) a buffer agent selected from the group consisting of citrate buffer, borax-citrate buffer, and citrate acid-phosphate buffer;
   (iii) an alkaline agent selected from the group consisting of sodium carbonate, potassium carbonate, sodium hydroxide, potassium hydroxide, and borate-sodium carbonate.

* * * * *